United States Patent [19]

Bell

[11] 4,069,337

[45] Jan. 17, 1978

[54] 2-SUBSTITUTED-INDOLE-1-LOWER-ALKANECARBOXAMIDES HAVING ANTI-SECRETORY OR ANTI-ULCER ACTIVITY

[75] Inventor: Malcolm R. Bell, East Greenbush, N.Y.

[73] Assignee: Sterling Drug Inc., New York, N.Y.

[21] Appl. No.: 746,516

[22] Filed: Dec. 1, 1976

Related U.S. Application Data

[62] Division of Ser. No. 624,334, Oct. 21, 1975, Pat. No. 4,021,448.

[51] Int. Cl.$^2$ .............................................. A61K 31/40
[52] U.S. Cl. ................................................... 424/274
[58] Field of Search ......................................... 424/274

[56] References Cited

U.S. PATENT DOCUMENTS 3,842,173   10/1974   Brenner et al. ...................... 424/274

Primary Examiner—Frederick E. Waddell
Attorney, Agent, or Firm—William G. Webb; B. Woodrow Wyatt

[57] ABSTRACT

2-Substituted-indole-1-lower-alkanecarboxamides, prepared by amidation of the corresponding acid or ester; by hydrolysis or thiohydrolysis of the corresponding carbonitrile; by alkylation of a suitable indole with a halo-lower-alkanecarboxamide; or by hydrolysis of a 1-indolechlorosulfonylcarbamyl derivative, have anti-secretory and anti-ulcer activities.

1 Claim, No Drawings

2-SUBSTITUTED-INDOLE-1-LOWER-ALKANECARBOXAMIDES HAVING ANTI-SECRETORY OR ANTI-ULCER ACTIVITY

RELATED APPLICATIONS

This is a division of my prior, copending application Ser. No. 624,334, filed Oct. 21, 1975, now U.S. Pat. No. 4,021,448, patented May 3, 1977.

BACKGROUND OF THE INVENTION a. Field of the Invention

This invention relates to 2-substituted-indole-1-lower-alkanecarboxamides useful as anti-secretory and anti-ulcer agents.

b. Description of the Prior Art

The compound 3-methyl-1-indoleacetamide, unsubstituted in the 2-position of the indole nucleus, is described by Swaminathan et al., J. Org. Chem. 22, 70–72 (1957), but no utility is suggested for the compound.

SUMMARY OF THE INVENTION

This invention relates, in one composition of matter aspect, to 2-$R_2$-3-$R_3$-5-$R_5$-1-indole-lower-alkanecarboxamides, having useful anti-secretory and anti-ulcer activities, where $R_2$, $R_3$ and $R_5$ have particular meanings more specifically described hereinbelow.

The invention also relates, in a second composition of matter aspect, to 2-$R_2$-3-$R_3$-5-$R_5$-1-indole-lower-alkanecarboxamides having a formyl group in either the 2- or 3-positions of the indole nucleus which are useful as intermediates for preparing the corresponding compounds having a hydroxymethyl in either the 2- or 3-positions.

The invention also relates, in a method aspect, to a method of reducing gastric secretion and incidence of ulcer formation in humans comprising administering an effective anti-secretory/anti-ulcer amount of a 2-$R_2$-3-$R_3$-5-$R_5$-1-indole-lower-alkanecarboxamide.

In one process aspect, the invention relates to a process for preparing a 2-$R_2$-3-$R_3$-5-$R_5$-1-indole-lower-alkanecarboxamide comprising reacting a mixed anhydride of a 2-$R_2$-3-$R_3$-5-$R_5$-1-indole-lower-alkanoic acid with an amine.

In another process aspect, the invention relates to a process for preparing a 2-$R_2$-3-$R_3$-5-$R_5$-1-indole-lower-alkanecarboxamide comprising reacting an acid halide of a 2-$R_2$-3-$R_3$-5-$R_5$-1-indole-lower-alkanoic acid with an amine.

In another process aspect, the invention relates to a process for preparing a 2-$R_2$-3-$R_3$-5-$R_5$-1-indole-lower-alkanecarboxamide comprising reacting a lower-alkyl 2-$R_2$-3-$R_3$-5-$R_5$-1-indole-lower-alkanoate with an amine.

In another process aspect, the invention relates to a process for preparing a 2-$R_2$-3-$R_3$-5-$R_5$-1-indole-lower-alkanecarboxamide comprising hydrolyzing a 2-$R_2$-3-$R_3$-5-$R_5$-1-indole-lower-alkanonitrile.

In another process aspect, the invention relates to a process for preparing a 2-$R_2$-3-$R_3$-5-$R_5$-1-indole-carboxamide comprising hydrolyzing a 2-$R_2$-3-$R_3$-5-$R_5$-1-halosulfonylcarbamylindole.

In another process aspect, the invention relates to a process for preparing a 2-$R_2$-3-$R_3$-5-$R_5$-1-indole-lower-alkanethiocarboxamide comprising reacting a 2-$R_2$-3-$R_3$-5-$R_5$-1-indole-lower-alkanonitrile with hydrogen sulfide in the presence of an alkali metal alkoxide.

In another process aspect, the invention relates to a process for preparing a 2-$R_2$-3-$R_3$-5-$R_5$-1-indole-lower-alkanecarboxamide wherein $R_2$ is hydroxymethyl and $R_3$ is hydroxymethyl or 2,2,2-trifluoro-1-hydroxyethyl comprising reducing with an alkali metal borohydride or with hydrogen over a palladium-on-charcoal catalyst a corresponding compound where $R_2$ or $R_3$ are, respectively, formyl or trifluoroacetyl.

DETAILED DESCRIPTION INCLUSIVE OF THE PREFERRED EMBODIMENTS

More specifically, this invention relates to 2-$R_2$-3-$R_3$-5-$R_5$-1-indole-lower-alkanecarboxamides having useful anti-secretory and anti-ulcer activities and having the formula:

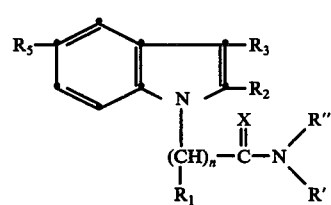

I where R' is hydrogen or methyl; R" is hydrogen, methyl or $(CH_2)_mOH$, where m is 0 (zero), 2 or 3; $R_1$ is hydrogen or methyl; $R_2$ is methyl, ethyl, phenyl or hydroxymethyl; $R_3$ is methyl, ethyl, hydroxymethyl, trifluoroacetyl or 2,2,2-trifluoro-1-hydroxyethyl; $R_5$ is hydrogen, chlorine or fluorine; X is O or S; and n is 0 (zero), 1, 2 or 3, n being 0 only when $R_5$ is chlorine.

Also within the ambit of the invention are certain compounds of the above formula I where either $R_2$ or $R_3$, instead of representing hydroxymethyl, represents formyl (CHO), the other values of $R_2$ and $R_3$ being the same as given above exclusive of hydroxymethyl. The formyl-substituted compounds are either inactive or only marginally active as anti-secretory or anti-ulcer agents but are useful as intermediates for the preparation of the corresponding compounds where the formyl group is reduced to the corresponding hydroxymethyl group. A particularly preferred group of compounds of this latter type are those wherein R', R" and $R_1$ are each hydrogen; $R_2$ is methyl or phenyl and $R_3$ is formyl, or $R_2$ is formyl and $R_3$ is methyl; $R_5$ is hydrogen or fluorine; X is O; and n is 1, 2 or 3.

The compounds of formula I are prepared by one of several methods involving amidation of the corresponding acid or ester; hydrolysis or thiohydrolysis of the corresponding carbonitrile; alkylation of an appropriate indole with a halo-lower-alkanecarboxamide in the presence of a strong base; or by hydrolysis of an N-chlorosulfonylcarbamyl derivative.

Thus, amidation of the corresponding carboxylic acid to produce the compounds of formula I were X is 0 comprises reacting the acid with a lower-alkyl halo-formate in the presence of an acid acceptor, and reacting the resulting mixed anhydride, without isolation, with an appropriate amine as represented by the reaction sequence:

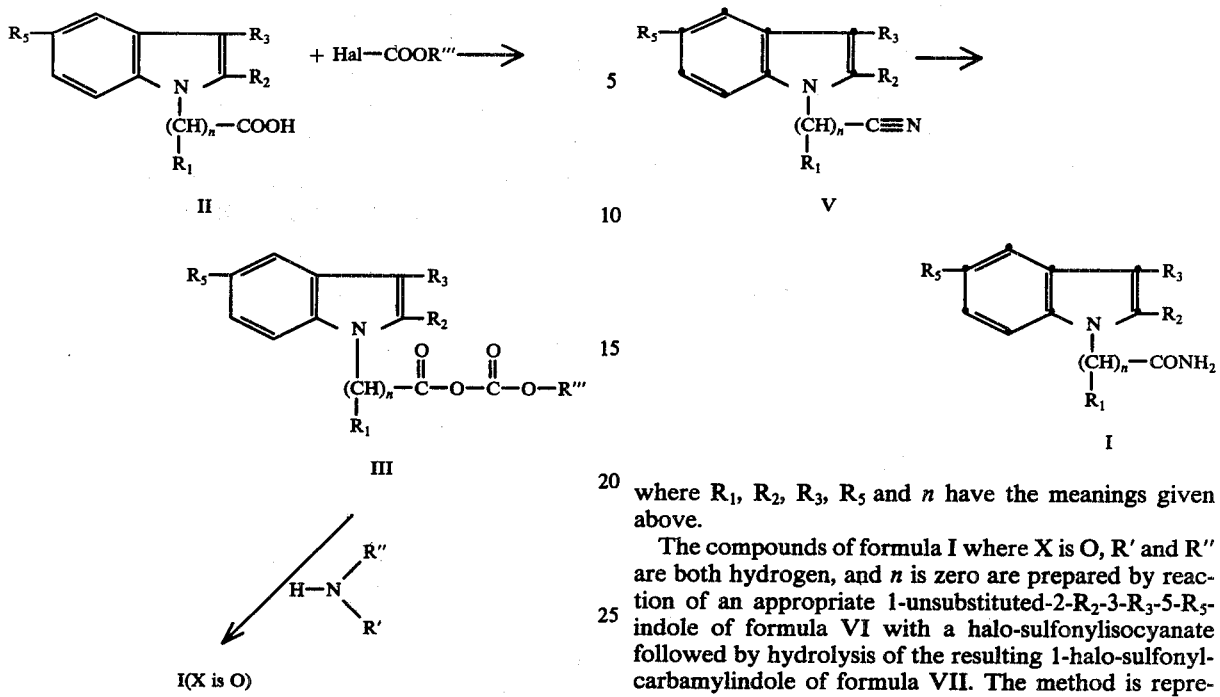

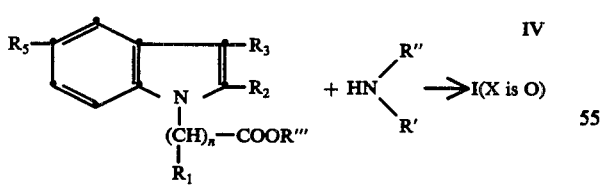

where R′, R″, $R_1$, $R_2$, $R_3$, $R_5$ and n have the meanings given above, Hal represents halogen, and R′″ represents lower-alkyl. The reaction is carried out at a temperature in the range from −10° to about 30° C. and in an inert organic solvent, for example chloroform, methylene dichloride, ethylene dichloride, benzene, toluene or diethyl ether.

Alternatively, the carboxylic acid can be converted to the corresponding acid halide by reacting the former with a thionyl halide or a phosphorus pentahalide, and reacting the resulting acid halide with an appropriate amine as before to give the compounds of formula I where X is O.

The procedure involving amidation of the ester to produce the compounds of formula I where X is O comprises heating a mixture of the ester and an appropriate amine, either with or without a solvent, at a temperature from 90° to about 150° C. as represented by the equation:

IV where R′, R″, R′″, $R_1$, $R_2$, $R_3$, $R_5$ and n have the meanings given above.

The compounds of formula I where X is O and R′ and R″ are each hydrogen are prepared by hydrolysis of the corresponding lower-alkanonitriles of formula V. The reaction is carried out by heating a solution of the carbonitrile in 90% aqueous sulfuric acid at a temperature in the range from 0° to 100° C. and is represented by the equation:

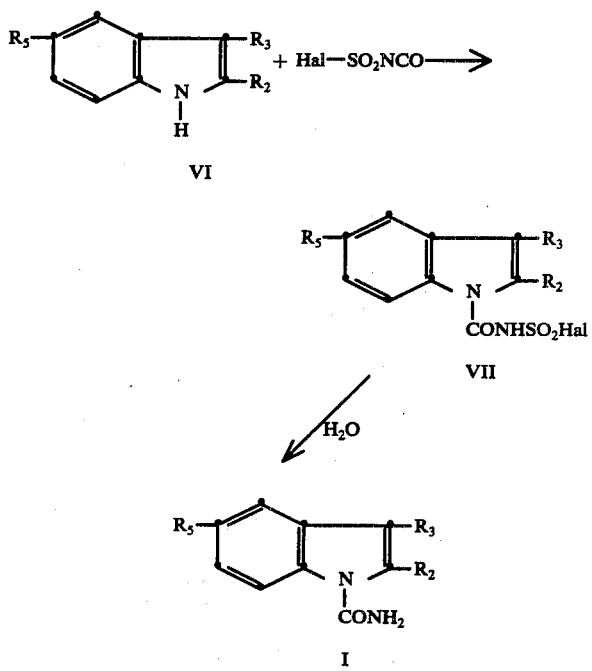

where $R_1$, $R_2$, $R_3$, $R_5$ and n have the meanings given above.

The compounds of formula I where X is O, R′ and R″ are both hydrogen, and n is zero are prepared by reaction of an appropriate 1-unsubstituted-2-$R_2$-3-$R_3$-5-$R_5$-indole of formula VI with a halo-sulfonylisocyanate followed by hydrolysis of the resulting 1-halo-sulfonyl-carbamylindole of formula VII. The method is represented by the reaction sequence:

where $R_2$, $R_3$, $R_5$ and Hal have the meanings given above.

The compounds of formula I where X is S are prepared by reaction of the corresponding lower-alkanonitriles of formula V with hydrogen sulfide in the presence of an alkali metal alkoxide. The reaction is preferably carried out by dissolving the nitrile in a solution of the alkoxide in excess lower-alkanol, saturating the resulting solution with hydrogen sulfide, and heating the solution in a pressure flask.

Finally, the compounds of formula I where $R_2$ or $R_3$ are hydroxymethyl or where $R_3$ is 2,2,2-trifluoro-1- hydroxyethyl are prepared by reducing the corresponding compound where $R_2$ or $R_3$ is formyl or where $R_3$ is trifluoroacetyl with an alkali metal borohydride or with hydrogen over a palladium-on-charcoal catalyst. Reduction with an alkali metal borohydride is advantageously carried out in a lower-alkanol solvent at a temperature in the range from 0° to 60° C., while catalytic reduction is carried out in a lower-alkanol solvent at a temperature from 20° to 50° C. and at hydrogen pressures of from 50 to 100 p.s.i.

The compounds of formulas II, IV, V and VI are generally known classes of compounds, and many examples are known in the art, although certain novel species of these compounds are required to prepare the compounds of the invention represented by formula I. The novel species are prepared by conventional methods well-known in the art.

Thus, the 2-$R_2$-3-$R_3$-5-$R_5$-indoles of formula VI are prepared using the Fisher indole synthesis which comprises reacting a 4-$R_5$-phenylhydrazine with an appropriate ketone having the formula:

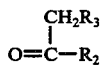

where $R_2$, $R_3$ and $R_5$ have the meanings given above.

The 2-$R_2$-3-$R_3$-5-$R_5$-1-indole-lower-alkanonitriles of formula V are prepared either by reaction of an appropriate 1-unsubstituted-indole of formula VI with an appropriate acrylonitrile in the presence of a strong base (to prepare the compounds where n is 2) or by reaction of a 1-unsubstituted-indole of formula VI with a halo-lower-alkanonitrile in the presence of a strong base such as an alkali metal hydride.

The esters of formula IV are prepared either by esterification of the corresponding carboxylic acids of formula II by conventional procedures or by reaction of a 1-unsubstituted-indole of formula VI with a lower-alkyl halo-lower-alkanoate in the presence of a strong base, for example an alkali metal hydride.

The 2-$R_2$-3-$R_3$-5-$R_5$-1-indole-lower-alkanoic acids of formula II are prepared by saponification of the corresponding esters which are prepared as described above.

In standard biological test procedures, described generally by Shay et al., Gastroenterology 5, 43 (1945) and 26, 906 (1954) and by Selmici et al., Acta Physiol. Acad. Sci. Hung. 25 (1), 101-104 (1964); C.A. 62, 2130b (1965), the compounds of formula I have been found to possess anti-secretory and anti-ulcer activities and are thus useful as anti-secretory and anti-ulcer agents. Anti-secretory activity was determined in male albino Wistar rats weighing approximately 180 g. using the method described by Shay et al. which is described as follows: the rats were divided into medicated groups of at least five rats each and control groups of ten rats. The rats were medicated orally once daily for 2 days prior to stomach ligation and once again immediately following ligation. All drugs were administered as the free base, and control rats received only the vehicle of medication. The rats were housed individually in wire cages, food was withdrawn 48 hours prior to surgery, and water was withdrawn at the time of surgery. Laparotomy was performed under light ether anesthesia, the pyloric-duodenal junction was ligated, and the wound was closed with metal clips and sprayed with a protective surgical dressing. Five hours following surgery, the rats were sacrificed, the stomach was removed, and the gastric juice collected. The gastric fluid was centrifuged, the total volume, color, and volume of solids were recorded. The pH of the gastric fluid was then determined on a Beckman pH meter, and the "free" and "total" hydrochloric acid content of each gastric sample was determined by titrating an aliquot of the gastric fluid (diluted to approximately 10 ml. with distilled water) by titrating with 0.1N sodium hydroxide against Toepfers reagent and phenolphthalein, respectively. By determining the milliequivalents of hydrochloric acid per milliliter of gastric juice and knowing the total volume of gastric juice secreted by each rat, the total acid output can be calculated. Since pH is a function of "free" acid, the activity of the test compounds can be evaluated by comparison of the mean "free" acid of medicated rats with the mean "free" acid of the controls, and the activity can thus be expressed in terms of percent inhibition of free acid.

The anti-ulcer activity of the compounds was determined using the reserpine-induced anti-ulcer test method, described by Selmici et al., which is described briefly as follows: male, albino, Sprague-Dawley rats, weighing approximately 300 g., were divided into medicated and control groups of at least five rats each, and one positive control group of five rats medicated with a known drug at the active dose was run with each experiment. The rats were medicated forty-eight, twenty-four, and one hour before receiving an injection of reserpine. All test drugs were administered orally in terms of base, and the control rats received only the vehicle of medication. The rats were housed individually in wire cages, and food was withdrawn 24 hours prior to injection of reserpine, while water was allowed ad libitum. One hour following the third medication, 5.0 mg. of reserpine per kilogram of body weight in a concentration of 5 mg./ml. was injected intramuscularly in each rat. Eighteen hours after injection the rats were sacrificed, their stomachs removed, opened along the greater curvature, rinsed in warm saline, and pinned to a cork board for gross observation. The stomachs were examined for the number and size of ulcerations located in the glandular portion of the stomach with the aid of a one millimeter grid ocular with a 10x dissecting microscope. The degree of ulceration was arbitrarily graded according to the number and size of the ulcers as follows:

0<1 mm.² 1 point
1<3 mm.² 2 points
≧3 mm.² 5 points.

The points were added together and divided by the number of rats in each group to give an ulcer score, and the difference in the mean scores of the medicated and control group was expressed as percent inhibition of ulceration. Alternatively, the results can be expressed as a ratio of the total number of rats with any degree of ulceration (as the numerator) to the total number of rats in the test group (as the denominator).

The compounds of formula I were thus found to inhibit secretion of gastric fluids and to inhibit reserpineinduced stomach ulceration when administered in a dose range of from around 10 mg./kg. to around 200 mg./kg. These results indicate usefulness of the compounds in humans as antisecretory/anti-ulcer agents when administered at a dose of 50 mg. per patient three or four times a day either alone or as the essential active ingredient. The compounds are preferably administered orally.

The actual determination of the numerical biological data definitive for a particular compound of formula I is readily determined by standard test procedures by technicians versed in pharmacological test procedures without the need for any extensive experimentation.

The compounds of formula I can be prepared for use by incorporation in unit dosage form as tablets or capsules for oral administration either alone or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

SPECIFIC EXEMPLARY DISCLOSURE

A. Preparation of Intermediates

Preparation 1

(The $2\text{-}R_2\text{-}3\text{-}R_3\text{-}5\text{-}R_5$-indoles of formula VI).

A solution of 1 g. (0.008 mole) of 4-fluorophenylhydrazine in 10 ml. of acetone was flushed with nitrogen, refluxed for ten minutes, and then taken to dryness in vacuo to leave 1.43 g. of the expected hydrazone as a golden yellow oil.

The latter was dissolved in 90 ml. of p-cymene, the flask was flushed with nitrogen, about 30 g. (0.22 mole) of zinc chloride was added, and the solution was refluxed for an hour. The solvent layer was decanted and taken to dryness in vacuo leaving 20.8 g. of a brown oil which was extracted with hexane and crystallized from the latter to give 6.7 g. of 5-fluoro-2-methylindole, m.p. 97°–98° C.

The latter (4.5 g., 0.03 mole) in 3 ml. of dimethylformamide (DMF) was added with stirring to a solution of 3 ml. (0.03 mole) of phosphorus oxychloride in 10 ml. of DMF while maintaining the temperature between 20° and 30° C. The solution was allowed to stand for two hours at ambient temperature, then poured over ice, and neutralized by the addition of a solution of 5.7 g. of sodium hydroxide in 30 ml. of water. The crystals which separated were collected, washed with water and recrystallized from methanol to give 2.7 g. of 2-methyl-3-formyl-5-fluoroindole, m.p. 217°–220° C.

Other known $2\text{-}R_2\text{-}3\text{-}R_3\text{-}5\text{-}R_5$-indoles of formula VI used in the preparation of the compounds of formula I are the following:

2-Methyl-3-formylindole disclosed by Beswas et al., Tetrahedron, 24 (3), 1145–1162 (1968);
2,3-Dimethyl-5-chloroindole disclosed by Rothstein et al., Compt. rend. 242, 1042–1043 (1956);
2-Ethyl-3-methylindole disclosed by Lesiak, Roczniki Chem. 36, 1097–1100 (1962); C.A. 58, 5615h (1963);
2-Methyl-3-ethylindole disclosed by McLean et al., Can. J. Chem. 49 (22), 3642–3647 (1971);
2-Phenyl-3-methylindole disclosed by Kanaoka et al., Chem. Pharm. Bull. (Tokyo) 14 (9), 934–939 (1966); and
2,3-Dimethylindole disclosed by VanDuuren, J. Org. Chem. 26, 2954–2960 (1961).

Preparation 2

(The $2\text{-}R_2\text{-}3\text{-}R_3\text{-}5\text{-}R_5$-1-indole-lower-alkanoic acids of formula II).

A. To a solution of 42 g. (0.29 mole) of 2,3-dimethylindole in 700 ml. of DMF was added 11.5 g. (0.29 mole) of a 60.1% dispersion of sodium hydride in mineral oil. The mixture was stirred at ambient temperature for one hour, cooled to 0° C. and then treated dropwise with stirring over a fifteen minute period with ethyl bromoacetate. The cooling bath was then removed, the mixture was stirred for two hours at room temperature, then poured into 2.5 liters of ice/water. The solid which separated was collected, washed with water, dissolved in 200 ml. of hot methanol and the solution treated with a solution of 30 g. of potassium hydroxide in 100 ml. of water. The resulting solution was refluxed for about two minutes, cooled, diluted to about 1600 ml. with water, filtered, and the filtrate acidified by the addition of concentrated hydrochloric acid to pH 2. The solid which separated was collected and recrystallized from benzene to give 9 g. of 2,3-dimethyl-1-indoleacetic acid, m.p. 186°–188° C.

B. A mixture of 4.5 g. (0.019 mole) of γ-(2-methyl-3-formyl-1-indole)butyramide (see Example 4J below), 3.5 g. (0.063 mole) of potassium hydroxide and 3 ml. of 85% aqueous hydrazine hydrate in 30 ml. of triethylene glycol was refluxed with stirring under a nitrogen atmosphere for three hours. The condenser was then removed until the temperature of the solution was raised to 200° C., the condenser was then replaced and the mixture heated for an additional 6 hours with stirring at 200° C. The resulting thick slurry was diluted with 30 ml. of water and acidified with dilute hydrochloric acid. The red solid which separated was filtered, washed with water and recrystallized from carbon tetrachloride to give 2.9 g. of γ-(2,3-dimethyl-1-indole)butyric acid, m.p. 102°–104° C.

C. To a stirred suspension of 27.0 g. of a 56% mineral oil dispersion of sodium hydride in 300 ml. of DMF was added, with cooling and stirring, a solution of 95.6 g. (0.6 mole) of 2-ethyl-3-methylindole in 300 ml. of DMF. The solution was stirred at room temperature for 1 hour, then cooled to −15° C. and treated with 72.3 ml. (0.65 mole) of ethyl bromoacetate. The product was isolated and saponified with 60 g. of potassium hydroxide in 500 ml. of methanol using the procedure described in Preparation 2A to give 87 g. of 2-ethyl-3-methyl-1-indoleacetic acid.

Also useful in the preparation of the compounds of formula I is the known compound β-(2,3-dimethyl-1-indole)-propionic acid disclosed by Almond et al., J. Chem. Soc. 1870–1874 (1952).

Preparation 3

(The lower-alkyl $2\text{-}R_2\text{-}3\text{-}R_3\text{-}5\text{-}R_5$-1-indole-lower-alkanoates of formula IV)

A. A solution of 50 g. (0.25 mole) of 2,3-dimethyl-1-indoleacetic acid in 250 ml. of absolute methanol was saturated with anhydrous hydrogen chloride and then refluxed for three hours. The solution was then taken to dryness, the residue partitioned between water and ethyl acetate, and the organic layer washed once with dilute sodium hydroxide, once with brine and then taken to dryness. The residual yellow brown solid was recrystallized twice from methanol to give 25 g. of methyl 2,3-dimethyl-1-indoleacetate, m.p. 88°–90° C.

B. Using a procedure similar to that described in Preparation 2, 143.3 g. (0.9 mole) of 2-methyl-3-ethylindole was alkylated with 150 g. (0.98 mole) of methyl bromoacetate in the presence of 40.5 g. (0.96 mole) of a 57% mineral oil dispersion of sodium hydride in 450 ml. of DMF. The product was isolated in the form of the ester which was recrystallized from chloroform/hexane to give two crops, 90 g., m.p. 91°–92° C. and 11 g., m.p. 88°–90° C., of methyl 2-methyl-3-ethyl-1-indoleacetate.

C. A solution of 99.3 g. (0.4 mole) of β-(2,3-dimethyl-1-indole)propionitrile (German Pat. No. 641597, published Feb. 11, 1937) in 200 ml. of methanol was cooled to −15° C. and saturated with anhydrous hydrogen chloride for about one hour. The solution was then refluxed for one half hour, allowed to stand overnight, and then poured onto ice and the mixture extracted with chloroform. The organic extracts were washed with aqueous sodium bicarbonate, dried over magnesium sulfate and concentrated to dryness to give 81 g. of crude material which was distilled in vacuo to give 78.5 g. of methyl β-(2,3-dimethyl-1-indole)propionate, b.p. 151°–158° C./0.4–0.7 mm., $n_D^{25.5}$ 1.5663.

Preparation 4

(The 2-$R_2$-3-$R_3$-5-$R_5$-1-indole)-lower-alkanonitriles of formula V)

A. A solution of 72 g. (0.4 mole) of 5-chloro-2,3-dimethylindole in 400 ml. of dioxane was treated with 28 ml. of acrylonitrile (0.43 mole), and 22.8 ml. of a 35% solution of benzyltrimethylammonium hydroxide in methanol was added and the solution allowed to stand for 2 days. The reaction mixture was poured into 1 liter of water and ice, neutralized with 30 ml. of concentrated hydrochloric acid, and the solid which separated was collected and recrystallized from isopropanol to give 78 g. of β-(5-chloro-2,3-dimethyl-1-indole)-propionitrile, m.p. 86°–88° C.

Other compounds of formula V similarly prepared were the following:

B. β-(2,3-Dimethyl-5-fluoro-1-indole)propionitrile (30 g., m.p. 85°–86° C. from isopropanol) prepared by reaction of 32.64 g. (0.2 mole) of 2,3-dimethyl-5-fluoroindole with 14 ml. of acrylonitrile in 200 ml. of dioxane in the presence of 11.4 ml. of 35% benzyltrimethylammonium hydroxide;

C. β-(2-Ethyl-3-methyl-1-indole)propionitrile (123.6 g.) prepared by reaction of 95.6 g. (0.6 mole) of 2-ethyl-3-methylindole with 42 ml. (0.64 mole) of acrylonitrile in 600 ml. of dioxane in the presence of 34.2 ml. of 35% benzyltrimethylammonium hydroxide;

D. β-(2-Methyl-3-ethyl-1-indole)propionitrile (114 g.) prepared by reaction of 95.6 g. (0.6 mole) of 2-methyl-3-ethylindole with 42 ml. (0.6 mole) of acrylonitrile in 600 ml. of dioxane in the presence of 34.2 ml. of 35% benzyltrimethylammonium hydroxide;

E. β-(2-Methyl-3-formyl-1-indole)propionitrile (51 g., m.p. 149°–150° C., from methylene dichloride) prepared by reaction of 69.2 g. (0.44 mole) of 2-methyl-3-formylindole with 30.5 ml. (0.46 mole) of acrylonitrile in 435 ml. of dioxane in the presence of 21.8 ml. of 35% benzyltrimethylammonium hydroxide;

F. β-(2-Phenyl-3-methyl-1-indole)propionitrile (17.7 g., m.p. 85°–87° C., from benzene/cyclohexane) prepared by reaction of 30 g. (0.15 mole) of 2-phenyl-3-methylindole with 11.2 ml. (0.17 mole) of acrylonitrile in 80 ml. of dioxane in the presence of 3 ml. of 35% benzyltrimethylammonium hydroxide.

G. β-(2-Methyl-3-formyl-5-fluoro-1-indole)propionitrile (29.4 g., m.p. 188°–190° C., from methylene dichloride) prepared by reaction of 28.2 g. (0.16 mole) of 2-methyl-3-formyl-5-fluoroindole with 18 ml. of acrylonitrile in 250 ml. of dioxane in the presence of 3 ml. of benzyltrimethylammonium hydroxide.

H. β-(3-Methyl-1-indole)propionitrile (155 g., m.p. 85°–90° C., from isopropanol) prepared by reaction of 200 g. (1.52 moles) of 3-methylindole with 107 ml. of acrylonitrile in 1.2 liters of dioxane in the presence of 88 ml. of 35% benzyltrimethylammonium hydroxide.

J. β-(2,3-Dimethyl-1-indole)-α-methylpropionitrile (30 g.) prepared by reaction of 36.3 g. (0.25 mole) of 2,5-dimethyl-indole with 17.8 g. (0.62 mole) of methacrylonitrile in 250 ml. of dioxane in the presence of 14.5 ml. of 35% benzyltrimethylammonium hydroxide.

K. γ-(2-Methyl-3-formyl-1-indole)butyronitrile (120 g., from benzene) prepared by reaction of 113 g. (0.71 mole) of 2-methyl-3-formylindole with 158 g. (1.07 mole) of 4-bromobutyronitrile in 1 liter of DMF in the presence of 37.5 g. (0.89 mole) of a 57% mineral oil dispersion of sodium hydride using the procedure described in Preparation 2A.

L. To a solution of 22.8 g. (0.12 mole) of β-(2-methyl-1-indole)propionitrile in a solution of 40 ml. of carbon tetrachloride and 19 ml. of DMF was added 25 ml. of trifluoroacetic anhydride while maintaining the temperature at −10° C. When addition was complete, the mixture was allowed to stand for about an hour at ambient temperature, then slurried with water, and the solid which had separated was collected and recrystallized from carbon tetrachloride to give 30.0 g. of β-(2-methyl-3-trifluoroacetyl-1-indole)-propionitrile, m.p. 108.5°–109.5° C.

M. To a solution of 33 ml. (0.36 mole) of phosphorus oxychloride in 96 ml. of DMF at 10–20° C. was added with stirring a solution of β-(3-methyl-1-indole)propionitrile in 180 ml. of DMF while maintaining the temperature at 15°–25° C. The solution was heated to 70°–75° C. for about 15 minutes, then cooled and poured into 600 ml. of ice water. The mixture was basified by the addition of a solution of 62.4 g. of sodium hydroxide in 360 ml. of water, and the solid which separated was collected, washed with water and recrystallized from methanol to give 51.5 g. of β-(2-formyl-3-methyl-1-indole)propionitrile.

N. A mixture of 60.5 g. (0.3 mole) of 2,3-dimethyl-1-indoleacetamide (described in Example 1A below), 120 g. (0.63 mole) of p-toluenesulfonyl chloride and 630 ml. of pyridine was heated on a steam bath for an hour, cooled and then poured into 4 liters of ice water. The solid which separated was collected, washed with water and dried to give 49 g. of 2,3-dimethyl-1-indoleacetonitrile, 84°–86° C.

Other known 1-indole-lower-alkanonitriles of formula V used in the preparation of the final products of formula I are:

β-(2-Methyl-1-indole)propionitrile disclosed in German Pat. No. 641597, published Feb. 11, 1937 and β-(2-Phenyl-3-formyl-1-indole)propionitrile disclosed by Blume et al., J. Org. Chem. 10, 255–258 (1945).

B. Preparation of the Final Products

EXAMPLE 1

A. To a solution of 22 g. (0.11 mole) of 2,3-dimethyl-1-indoleacetic acid and 15 ml. (0.11 mole) of triethylamine in 500 ml. of methylene dichloride at 0° C. was added 11.7 g. (0.11 mole) of ethyl chloroformate. The solution was stirred at 0° C. for a half hour, and then treated with an excess of a solution of ammonia in 300 ml. of methylene dichloride. The mixture was then stirred at ambient temperature for an hour and a quarter. The reaction mixture was extracted once with water, once with aqueous sodium bicarbonate and once with brine, then dried and evaporated to a volume of about 25 ml. and diluted with 50 ml. of hot hexane. There was thus obtained 9 g. of material which was recrystallized from ethyl acetate to give 6.8 g. of 2,3-dimethyl-1-indoleacetamide, m.p. 197°–199° C.

Other compounds of formula I which were prepared using a procedure similar to that described in Example 1A are as follows:

B. 2,3-Dimethyl-1-indole-N-methylacetamide (34.3 g., m.p. 187°–190° C., from methanol) prepared by reaction of 50 g. (0.24 mole) of 2,3-dimethyl-1-indoleacetic acid with 25.7 ml. (0.27 mole) of ethyl chloroformate and 37.8 ml. (0.27 mole) of triethylamine in 1 liter of methylene dichloride and reaction of the resulting mixed anhydride with methylamine;

C. 2-Ethyl-3-methyl-1-indoleacetamide (16.5 g., m.p. 161°–162° C, from benzene) prepared by reaction of 43.45 g. (0.2 mole) of 2-ethyl-3-methyl-1-indoleacetic acid with 19 ml. (1.1 mole) of ethyl chloroformate and 78 ml. (0.2 mole) of triethylamine in 600 ml. of methylene dichloride and reaction of the resulting mixed anhydride with ammonia;

D. γ-(2,3-Dimethyl-1-indole)butyramide (16.3 g., m.p. 132°–134° C., from ethyl acetate) prepared by reaction of 23.1 g. (0.1 mole) of γ-(2,3-dimethyl-1-indole)butyric acid with 13.6 g. (0.1 mole) of isobutyl chloroformate and 14.7 ml. (0.11 mole) of triethylamine in 400 ml. of chloroform and reaction of the resulting mixed anhydride with ammonia.

EXAMPLE 2

To a solution of 10.85 g. (0.05 mole) of β-(2,3-dimethyl-1-indole)propionic acid in 250 ml. of dry ether was added 10.43 g. (0.50 mole) of phosphorus pentachloride, and the solution was stirred for a half hour at −5° C., then for an additional hour at ambient temperature and poured into 200 ml. of 40% aqueous dimethylamine containing 200 g. of ice. After standing overnight, the organic layer was separated, the aqueous layer was extracted with ether and the combined ether extracts dried and concentrated to dryness to give 12 g. of a crude oil which crystallized to give 8.1 g. of β-(2,3-dimethyl-1-indole)-N,N-dimethylpropionamide, m.p. 73°–74° C.

EXAMPLE 3

A. A mixture of 20 g. (0.092 mole) of methyl 2,3-dimethyl-1-indoleacetate and 100 ml. of ethanolamine was heated on a steam bath for 3 hours, then poured into 3 liters of water, and the resulting solid collected by filtration and recrystallized from benzene to give 18.9 g. of 2,3-dimethyl-1-indole-N-(2-hydroxyethyl)acetamide, m.p. 156°–158° C.

Other compounds of formula I which were prepared using a procedure similar to that described in Example 3A are as follows:

B. 2,3-Dimethyl-1-indoleacetohydroxamic acid (12.1 g., m.p. 168° C., dec., from acetonitrile) prepared by reaction of 21.7 g. (0.1 mole) of methyl 2,3-dimethyl-1-indoleacetate with 14.2 g. (0.2 mole) of hydroxylamine hydrochloride in 75 ml. of methanol in the presence of a solution of 17 g. (0.3 mole) of potassium hydroxide in 45 ml. of methanol;

C. 2-Methyl-3-ethyl-1-indoleacetamide (10.1 g., m.p. 168°–169° C., from ethanol) prepared by reaction of 40 g. (0.17 mole) of methyl 2-methyl-3-ethyl-1-indoleacetate with 700 ml. of a saturated solution of ammonia in ethanol;

D. β-(2,3-Dimethyl-1-indole)-N-(2-hydroxyethyl)propionamide (20.8 g., m.p. 89°–90° C., from benzene) prepared by reaction of 20.8 g. (0.09 mole) of methyl β-(2,3-dimethyl-1-indole)-propionate with 100 ml. of ethanolamine;

E. β-(2,3-Dimethyl-1-indole)-N-(3-hydroxypropyl)propionamide (19.2 g., m.p. 89°–90° C., from benzene) prepared by reaction of 20.8 g. (0.09 mole) of methyl β-(2,3-dimethyl-1-indole)-propionate with 70 ml. of 3-hydroxypropylamine;

F. β-(2,3-Dimethyl-1-indole)propionohydroxamic acid (22.5 g., m.p. 137°–138° C., from acetonitrile) prepared by reaction of 34 g. (0.14 mole) of methyl β-(2,3-dimethyl-1-indole)propionate with 20.4 g. (0.29 mole) of hydroxylamine hydrochloride in 105 ml. of methanol in the presence of 28.4 g. (0.44 mole) of potassium hydroxide in 70 ml. of methanol.

EXAMPLE 4

A. A solution of 10.7 g. (0.05 mole) of β-(2,3-dimethyl-1-indole)propionitrile in a solution of 1.5 ml. of water and 15 ml. of concentrated sulfuric acid was heated with stirring on a steam bath for ten hours and then poured into 200 ml. of ice water and extracted with chloroform. The organic extracts were washed with dilute ammonium hydroxide, then with water, dried and concentrated to dryness to give 11.5 g. of a yellow gum which was recrystallized from benzene to give 9.5 g. of β-(2,3-dimethyl-1-indole)propionamide, m.p. 106°–107° C.

Other compounds of formula I prepared using a procedure similar to that described in Example 4A are as follows:

B. β-(2,3-Dimethyl-5-chloro-1-indole)propionamide (34 g., m.p. 138°–139° C., from carbon tetrachloride) prepared by hydrolysis of 46.54 g. (0.2 mole) of β-(2,3-dimethyl-5-chloro-1-indole)propionitrile in 66 ml. of 90% aqueous sulfuric acid;

C. β-(2,3-Dimethyl-5-fluoro-1-indole)propionamide (9.5 g., m.p. 122°–123° C., from carbon tetrachloride) prepared by hydrolysis of 29.8 g. (0.18 mole) of β-(2,3-dimethyl-5-fluoro-1-indole)propionitrile in 66 ml. of 90% aqueous sulfuric acid;

D. β-(2-Ethyl-3-methyl-1-indole)propionamide (29.8 g., m.p. 110°–111° C., from benzene/cyclohexane) prepared by hydrolysis of 63.69 g. (0.3 mole) of β-(2-ethyl-3-methyl-1-indole)propionitrile in 88 ml. of 90% aqueous sulfuric acid;

E. β-(2-Methyl-3-ethyl-1-indole)propionamide (39 g., m.p. 90°–91° C., from benzene/cyclohexane) prepared by hydrolysis of 63.69 g. (0.3 mole) of β-(2-methyl-3-ethyl-1-indole)-propionitrile in 88 ml. of 90% aqueous sulfuric acid;

F. β-(2-Methyl-3-formyl-1-indole)propionamide (40.1 g., m.p. 201°-202° C., from methanol) prepared by hydrolysis of 49.7 g. (0.23 mole) of β-(2-methyl-3-formyl-1-indole)propionitrile in a solution of 66 ml. of 90% aqueous sulfuric acid;

G. β-(2-Methyl-3-formyl-5-fluoro-1-indole)propionamide (23.1 g., m.p. 238°-239° C., from methanol) prepared by hydrolysis of 27.1 g. (0.12 mole) of β-(2-methyl-3-formyl-5-fluoro-1-indole)propionitrile in 36 ml. of 90% aqueous sulfuric acid;

H. β-(2,3-Dimethyl-1-indole)-α-methylpropionamide (11.7 g., m.p. 107.5°-110° C., from ethyl acetate/cyclohexane) prepared by hydrolysis of 30 g. (0.14 mole) of β-(2,3-dimethyl-1-indole)-α-methylpropionitrile in 55 ml. of 90% aqueous sulfuric acid;

J. γ-(2-Methyl-3-formyl-1-indole)butyramide (63.6 g., m.p. 178.5°-180° C., from ethanol) prepared by hydrolysis of 75 g. (0.33 mole) of γ-(2-methyl-3-formyl-1-indole)-butyronitrile in 110 ml. of 90% aqueous sulfuric acid;

K. β-(2-Formyl-3-methyl-1-indole)propionamide (7.5 g., m.p. 166°-167° C., from methanol) prepared by hydrolysis of 42.5 g. (0.20 mole) of β-(2-formyl-3-methyl-1-indole)propionitrile in 200 ml. of 90% aqueous sulfuric acid;

L. β-(2-Methyl-3-trifluoroacetyl-1-indole)propionamide (8.3 g., m.p. 158°-159° C., from methylene dichloride) prepared by hydrolysis of 20 g. (0.07 mole) of β-(2-methyl-3-trifluoroacetyl-1-indole)propionitrile in 44 ml. of 90% aqueous sulfuric acid;

M. β-(2-Phenyl-3-methyl-1-indole)propionamide (5.6 g., m.p. 136°-137° C., from benzene/cyclohexane) prepared by hydrolysis of 17.7 g. (0.068 mole) of β-(2-phenyl-3-methyl-1-indole)propionitrile in 21 ml. of 90% aqueous sulfuric acid;

N. β-(2-Phenyl-3-formyl-1-indole)propionamide (2.3 g., m.p. 218°-219° C., from methanol) prepared by hydrolysis of 9 g. (0.03 mole) of β-(2-phenyl-3-formyl-1-indole)propionitrile in 33 ml. of 90% aqueous sulfuric acid.

EXAMPLE 5

To a solution of 36 g. (0.2 mole) of 2,3-dimethyl-5-chloroindole in 300 ml. of methylene dichloride was added 8 ml. of chlorosulfonylisocyanate. An additional 300 ml. of methylene dichloride was added followed by an additional 9.3 ml. of chlorosulfonylisocyanate, and the solution was stirred for several minutes, then diluted with 500 ml. of pentane and filtered. The solid material was dissolved in about 300 ml. of acetone, and the solution was cooled in an ice bath and carefully diluted, with stirring, with about 20 ml. of water. When the exothermic reaction had subsided, another 30 ml. of water was added, the mixture was allowed to stand at ambient temperature for several minutes, then diluted with 800 ml. of water and filtered. The solid material was recrystallized once from methanol to give 24.7 g. of 2,3-dimethyl-5-chloro-1-indolecarboxamide, m.p. 201°-203° C.

EXAMPLE 6

A solution of 95.6 g. (0.6 mole) of 2-methyl-3-formylindole in 250 ml. of DMF was added to a suspension of 28 g. (0.66 mole) of a 56% mineral oil dispersion of sodium hydride in 50 ml. of DMF, and the solution was cooled to about 20° C. and stirred for one hour. The solution was then cooled to −10° C. and treated all at once with a solution of 60 g. (0.64 mole) of α-chloroacetamide in 200 ml. of DMF. The solution was allowed to warm to ambient temperature and then was heated on a steam bath for a few minutes and finally was cooled and poured into 1500 ml. of ice water. The solid which separated was collected and dried to give 112 g. of 2-methyl-3-formyl-1-indoleacetamide, m.p. 250°-252° C. A small sample recrystallized from DMF/methanol gave material having m.p. 256-257° C.

EXAMPLE 7

A. A solution of 20 g. (0.11 mole) of 2,3-dimethyl-1-indoleacetonitrile in 100 ml. of absolute ethanol containing 200 mg. of sodium methoxide was saturated with hydrogen sulfide, and the solution was heated in a pressure flask on a steam bath for six hours and then allowed to cool to ambient temperature overnight. The reaction mixture was poured into ice water and the mixture extracted with ethyl acetate. Evaporation of the organic extracts to dryness and recrystallization of the residue from ethanol gave 18.8 g. of 2,3-dimethyl-1-indolethioacetamide, m.p. 168°-171° C.

B. Following a procedure similar to that described in Example 7A, 12 g. of β-(2,3-dimethyl-1-indole)propionitrile in 100 ml. of absolute ethanol containing 0.3 g. of sodium methoxide was saturated with hydrogen sulfide, and the solution was heated in a pressure bottle at 80° C. for six hours. The crude product thus obtained was recrystallized from ethanol to give 4.0 g. of β(2,3-dimethyl-1-indole)thiopropionamide, m.p. 119°-120° C.

EXAMPLE 8

A. A solution of 46.0 g. (0.2 mole) of β-(2-methyl-3-formyl-1-indole)propionamide dissolved in 3 liters of absolute ethanol was cooled, treated with 25.7 g. (0.6 mole) of sodium borohydride, and the mixture heated slowly on a steam bath until all material had dissolved. The solution was refluxed for a half hour, filtered, concentrated in vacuo to 600 ml. and rendered basic by the addition of a solution of 80 ml. of 35% sodium hydroxide in 920 ml. of water. The material, which slowly recrystallized on seeding and scratching, was collected, washed with water and recrystallized from ethanol to give 22 g. of β-(2-methyl-3-hydroxymethyl-1-indole)-propionamide, m.p. 155° C.

Other compounds of formula I prepared using a procedure similar to that described in Example 8A are as follows:

B. γ-(2-Methyl-3-hydroxymethyl-1-indole)butyramide (8.8 g., m.p. 110°-112.5° C., from ethyl acetate) prepared by reduction of 24.4 g. (0.1 mole) of γ-(2-methyl-3-formyl-1-indole)-butyramide with 12.9 g. of sodium borohydride in 1.5 liters of absolute ethanol;

C. 2-Methyl-3-hydroxymethyl-1-indoleacetamide (13.4 g., m.p. 181°-182° C., from methanol) prepared by reduction of 21.62 g. (0.1 mole) of 2-methyl-3-formyl-1-indoleacetamide with 14.36 g. (0.3 mole) of sodium borohydride in 1500 ml. of absolute ethanol;

D. β-(2-Phenyl-3-hydroxymethyl-1-indole)propionamide (4.22 g., m.p. 141°-142° C., from ethanol) prepared by reduction of 6.7 g. (0.023 mole) of β-(2-phenyl-3-formyl-1-indole)propionamide with 3.34 g. (0.07 mole) of sodium borohydride in absolute ethanol;

E. β-(2-Methyl-3-hydroxymethyl-5-fluoro-1-indole)-propionamide (8.9 g., m.p. 157°-157.5° C., from isopropanol) prepared by reduction of 16.1 g. (0.065 mole) of β-(2-methyl-3-formyl-5-fluoro-1-indole)propionamide with 7.6 g. (0.2 mole) of sodium borohydride in methanol;

F. β-[2-Methyl-3-(2-trifluoro-1-hydroxyethyl)-1-indole]-propionamide (7.8 g., m.p. 138°-140° C., from methylene dichloride) prepared by reduction of 8 g. (0.027 mole) of β-(2-methyl-3-trifluoroacetyl-1-indole)-propionamide with 2.08 g. (0.06 mole) of sodium borohydride and 6.1 g. (0.08 mole) of ammonium acetate in ethanol.

G. To a solution of 15.85 g. (0.069 mole) of β-(2-formyl-3-methyl-1-indole)propionamide in 1800 ml. of absolute ethanol was added 1 g. of 10% palladium-on-charcoal, and the mixture was reduced with hydrogen at 50° C. for 12 hours under a hydrogen pressure of 400 p.s.i. The catalyst was then removed by filtration and the filtrate taken to dryness to give a solid residue which was recrystallized from ethyl acetate to give 1.6 g. of β-(2-hydroxymethyl-3-methyl-1-indole)propionamide, m.p. 180°-181° C.

BIOLOGICAL TEST RESULTS

Data obtained on administration of the compounds of formula I in rats in the anti-secretory and anti-ulcer tests described above are given in the table below. Unless noted otherwise, data were obtained on oral administration. Results in the anti-secretory activity tests are given in terms of the pH of the gastric fluid in the test animals and the percent inhibition of free acid, while results in the anti-ulcer test are given either in terms of the percent inhibition of ulcers or as a ratio representing the number of animals with ulcers (as the numerator) to the total number of animals in the test group (as the denominator). All doses are expressed in mg./kg. For reference purposes, results obtained in similar tests on the known reference compound, 3-methyl-1-indole-acetamide, designated "Reference", which I have found also has anti-secretory and anti-ulcer activities, are given for purposes of comparison.

| Example | Dose | Anti-Secretory pH | % Inhibition of Free Acid | Anti-Ulcer % Inhibition |
|---|---|---|---|---|
| Reference | 100 | 2.3 | 62 | 75 |
| 1A | 0.8 | — | — | 0 |
|  | 1.56 | — | — | 38 |
|  | 3.12 | — | — | 45 |
|  | 6.25 | — | — | 75 |
|  | 12.5 | — | — | 81 |
|  | 25 | 2.6 | 69 | 95 |
|  | 50 | 3.0 | 65 | 98 |
|  | 100 | 6.0 | 100 | 99 |
|  | 200 | 6.7 | 100 | — |
| 1B | 6.25(i.d.) | 1.4 | 46 | — |
|  | 50(s.c.) | — | — | 93 |
|  | 100 | 1.8 | 45 | 91 |
| 1C | 25 | — | — | 84 |
|  | 100 | 2.8 | 50 | 96 |
| 1D | 0.8 | — | — | 38 |
|  | 1.56 | — | — | 38 |
|  | 6.25 | 1.3 | 14 | 0 |
|  | 25 | 1.6 | 38 | 72 |
|  | 100 | 6.2 | 100 | 99 |
| 2 | 25 | — | — | 34 |
|  | 100 | 4.4 | 93 | — |
| 3A | 50(s.c.) | — | — | 69 |
|  | 100 | 1.4 | 22 | 84 |
| 3B | 100 | 1.4 | 20 | 99 |
|  | 100 | 1.8 | 38 | — |
| 3C | 100 | 2.8 | 86 | 97 |
| 3D | 25 | — | — | 48 |
|  | 100 | 1.2 | — | — |
| 3E | 25 | — | — | 51 |
|  | 100 | 1.4 | 34 | — |
| 3F | 50 | — | — | 95 |
|  | 100 | 1.3 | 34 | — |
| 4A | 1.56 | — | — | 43 |
|  | 6.25 | — | — | 48 |
|  | 25 | — | — | 93 |
|  | 50(s.c.) | — | — | 89 |
|  | 100 | 5.3 | 100 | — |

-continued

| Example | Dose | Anti-Secretory pH | % Inhibition of Free Acid | Anti-Ulcer % Inhibition |
|---|---|---|---|---|
| 4B | 25 | — | — | 95 |
|  | 100 | 3.6 | 88 | — |
| 4C | 25 | — | — | 94 |
|  | 100 | 5.9 | 97 | — |
| 4D | 100 | 4.1 | 88 | 97 |
| 4E | 6.25 | — | — | 60 |
|  | 12.5 | — | — | 72 |
|  | 25 | — | −80 | — |
|  | 50 | — | — | 94 |
|  | 100 | 3.4 | 42 | 93 |
| 4F | 100 | 1.2 | 0 | 9 |
| 4G | 100 | 1.1 | 17 | 5/5 |
|  | 100(s.c.) | 1.2 | 36 | — |
| 4H | 100 | 5.7 | 100 | 89 |
| 4J | 100 | 1.2 | 17 | 26 |
| 4K | 100 | 1.16 | — | 3/5 |
|  | 100(i.p.) | 2.30 | 54 | — |
|  | 100(i.d.) | 1.54 | 37 | — |
| 4L | 100 | 1.8 | 46 | — |
|  | 100(i.p.) | 3.8 | 78 | — |
|  | 100(i.d.) | 2.5 | 65 | — |
| 4M | 100 | 1.1 | 20 | 0/5 |
|  | 100(i.d.) | 1.2 | 34 | — |
|  | 100(i.p.) | 1.7 | 43 | — |
| 4N | 100 | 1.0 | 0 | 5/5 |
|  | 100(s.c.) | 1.0 | 0 | — |
| 5 | 25 | — | — | 0 |
|  | 100 | 2.0 | 41 | — |
| 6 | 100 | 1.1 | 0 | 0 |
| 7A | 25 | — | — | 75 |
|  | 100 | 2.3 | 58 | — |
| 7B | 100 | 2.2 | 60 | 100 |
| 8A | 100 | 1.9 | 69 | 56 |
|  | 100(i.d.) | 5.6 | 100 | — |
|  | 100(s.c.) | 6.7 | 100 | — |
|  | 100(i.p.) | 7.0 | 100 | — |
| 8B | 100 | 1.3 | 5 | 0 |
|  | 100(i.d.) | 1.2 | 5 | — |
|  | 100(s.c.) | 1.2 | 12 | — |
|  | 100(i.p.) | 2.4 | 62 | — |
| 8C | 50(s.c.) | — | — | 0/5 |
|  | 100 | 1.5 | 62 | — |
|  | 100(s.c.) | 6.9 | 100 | — |
|  | 100(i.d.) | 1.1 | 30 | — |
|  | 100(i.p.) | 2.0 | 61 | — |
| 8D | 100 | 1.5 | 28 | 0/5 |
|  | 100(s.c.) | 1.4 | 38 | — |
| 8E | 50(s.c.) | — | — | 1/3 |
|  | 100 | 1.1 | 22 | — |
|  | 100(s.c.) | 6.1 | 100 | — |
|  | 100(i.p.) | 5.9 | 100 | — |
|  | 100(i.d.) | 3.5 | 89 | — |
| 8F | 50 | — | — | 45 |
|  | 100 | 1.0 | 2 | — |
|  | 100(s.c.) | 1.0 | 7 | — |
|  | 100(i.p.) | 1.2 | 24 | — |
|  | 100(i.d.) | 1.5 | 69 | — |
| 8G | 100 | 1.3 | 22 | 3/5 |
|  | 100(i.p.) | 1.7 | 34 | — |
|  | 100(i.d.) | 1.4 | 33 | — |

I claim:
1. A method of reducing gastric secretion and incidence of ulcer formation in humans comprising orally administering thereto an effective anti-secretory or anti-ulcer amount of a 2-$R_2$-3-$R_3$-5-$R_5$-1-indole-lower-alkanecarboxamide having the formula:

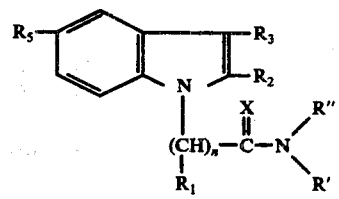

where R' is hydrogen or methyl; R" is hydrogen, methyl or $(CH_2)_m OH$, where m is 0, 2 or 3; $R_1$ is hydrogen or methyl; $R_2$ is methyl, ethyl, phenyl or hydroxymethyl; $R_3$ is methyl, ethyl, hydroxymethyl, trifluoroacetyl or 2,2,2-trifluoro-1hydroxyethyl; $R_5$ is hydrogen, chlorine or fluorine; X is O or S; and n is 0, 1, 2 or 3, n being 0 only when $R_5$ is chlorine.

* * * * *